United States Patent [19]

Goldberg et al.

[11] Patent Number: 4,620,846
[45] Date of Patent: Nov. 4, 1986

[54] APPARATUS AND METHOD FOR INTRODUCING FLUID INTO AND REMOVING FLUID FROM A LIVING SUBJECT

[76] Inventors: Edward M. Goldberg, 225 Maple Hill Rd., Glencoe, Ill. 60022; Seymour Bazell, 9235 N. Latrobe, Skokie, Ill. 60077

[21] Appl. No.: 572,821

[22] Filed: Jan. 23, 1984

Related U.S. Application Data

[60] Division of Ser. No. 307,188, Sep. 30, 1981, Pat. No. 4,435,171, which is a continuation of Ser. No. 45,294, Jun. 4, 1979, abandoned.

[51] Int. Cl.[4] ............................................. A61M 1/00
[52] U.S. Cl. ........................................ 604/28; 604/29; 604/410
[58] Field of Search ................. 604/27, 28, 29, 30, 604/32, 33, 34, 46, 48, 49, 51, 52, 53, 54, 80, 81, 317; 128/760, 762, 766, 767; 210/645

[56] References Cited

U.S. PATENT DOCUMENTS

| | | | |
|---|---|---|---|
| 1,683,723 | 9/1928 | Myres | 604/80 |
| 3,424,218 | 1/1969 | Vanderbur et al. | 150/0.5 |
| 3,848,581 | 11/1974 | Cinqualbre et al. | 128/766 |
| 4,239,041 | 12/1980 | Popovich et al. | 128/213 A |

Primary Examiner—C. Fred Rosenbaum
Assistant Examiner—J. L. Kruter
Attorney, Agent, or Firm—Hosier & Sufrin, Ltd.

[57] ABSTRACT

Manifolds are disclosed for introducing fluid into the human body and removing fluid therefrom. The fluid removing manifolds include a plurality of separately valved containers sealed to the manifold. Each container is filled in series via the manifold and the associated valve is closed before the container is removed from the manifold for disposal. Thus, a closed drainage system is provided. The fluid introducing manifolds include a plurality of separately valved input ports. Preferably, each port is used only once to reduce contamination of the manifold and associated infection. In each case, the port is kept closed until it is coupled to a source of fluid, and it is reclosed before the source of fluid is disconnected from the port. In this way, contamination is further reduced. Both the multiple input port feature and the multiple container feature of the invention are incorporated in manifolds for use with peritoneal dialysis.

5 Claims, 16 Drawing Figures

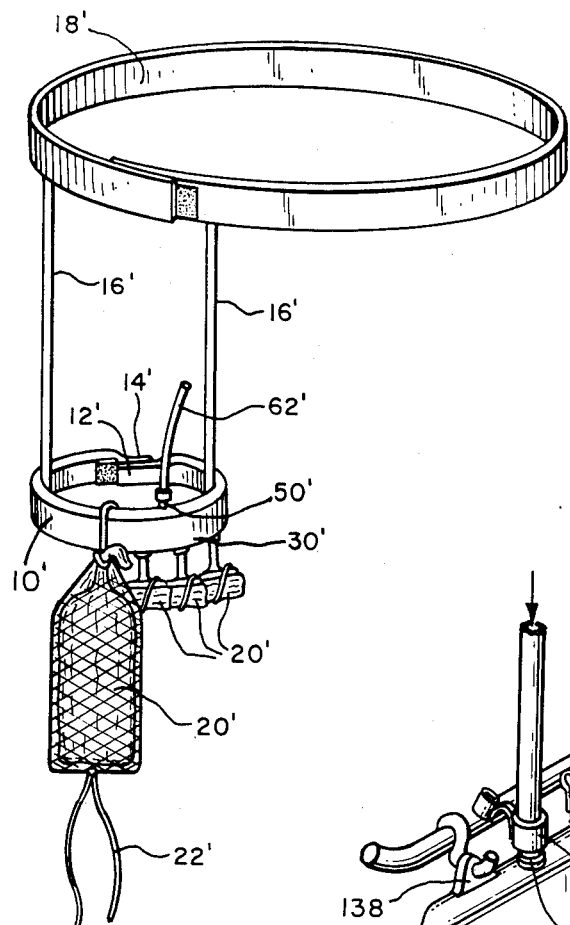
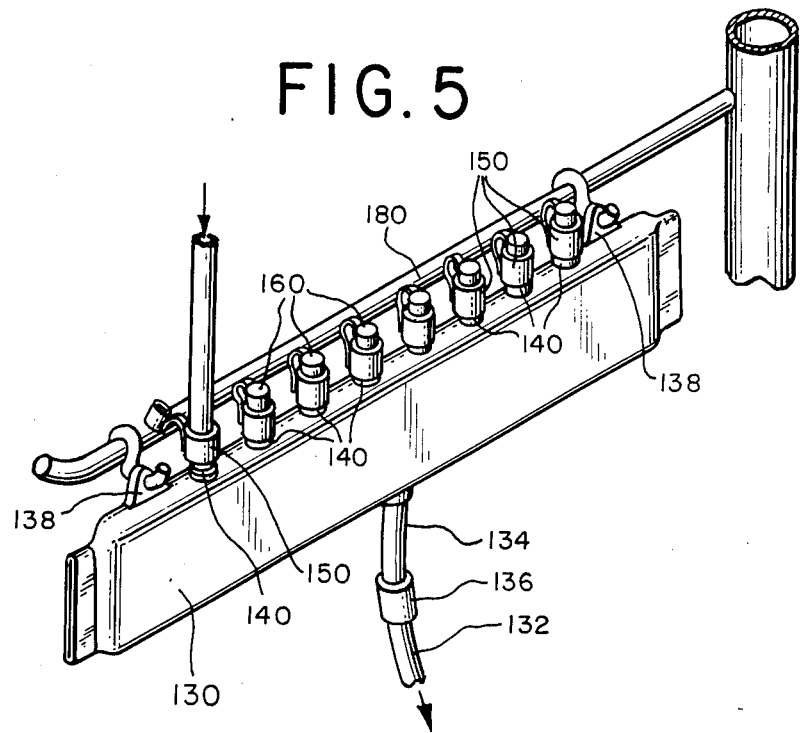
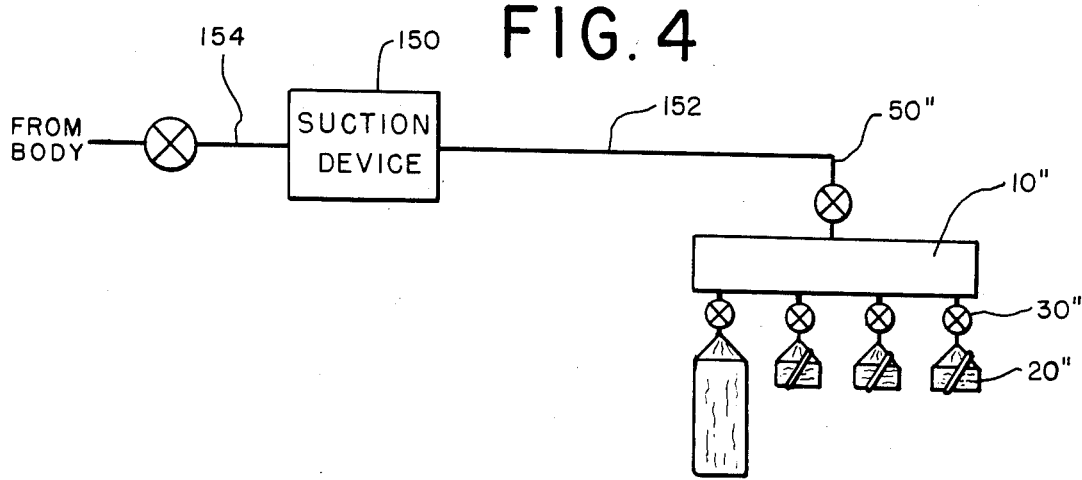

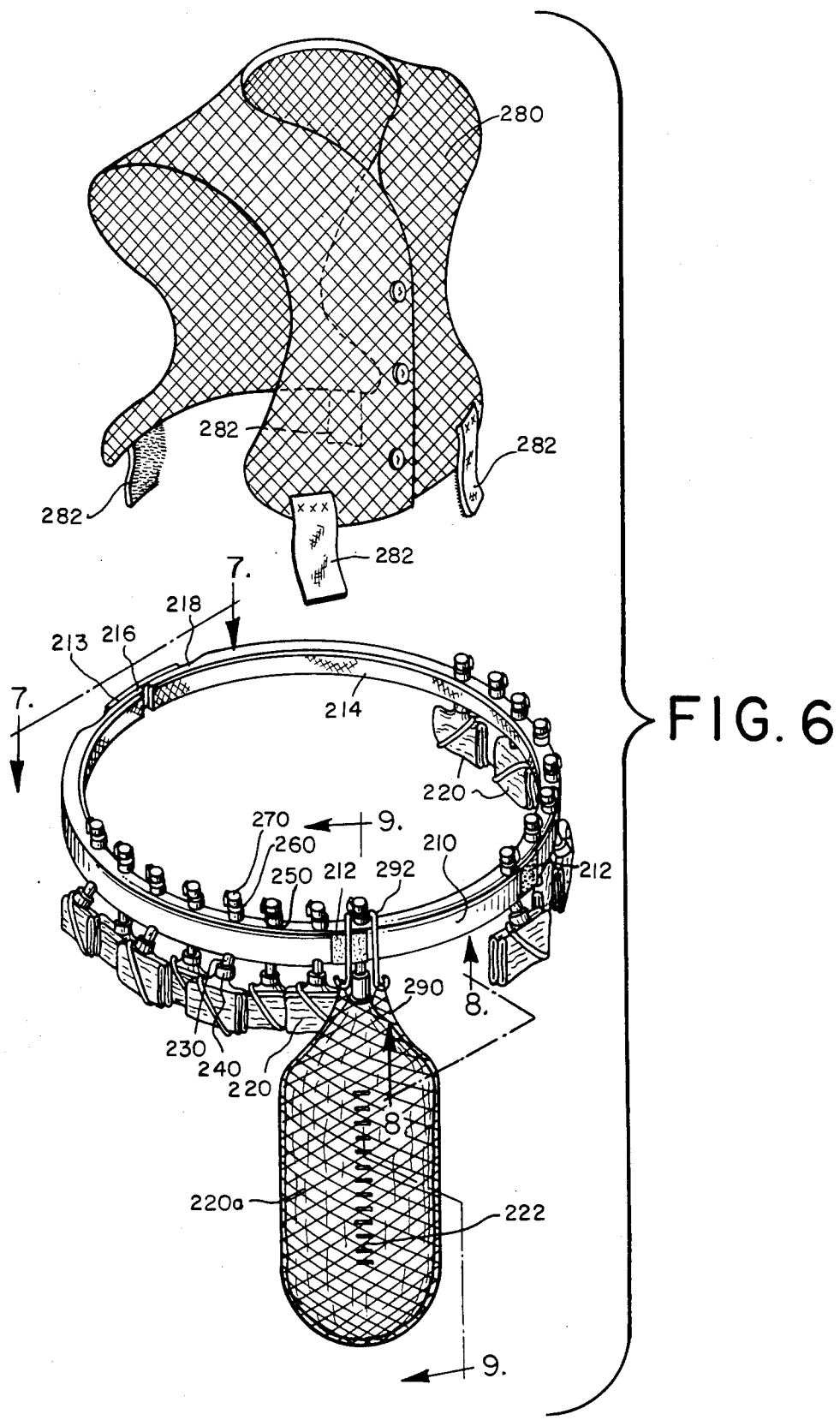

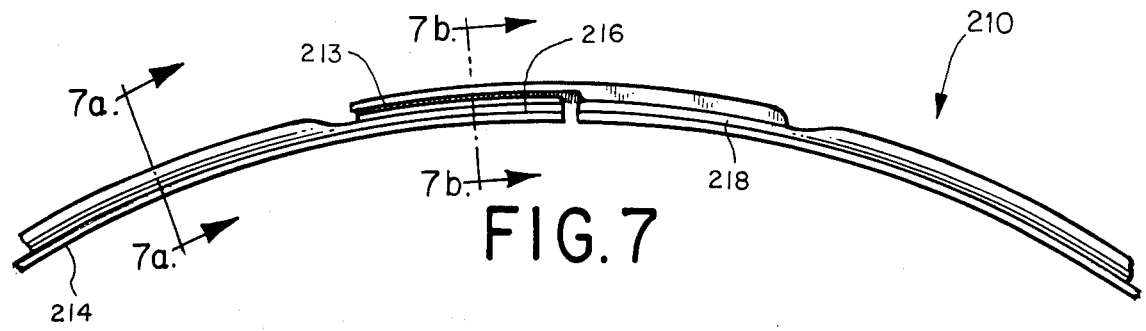
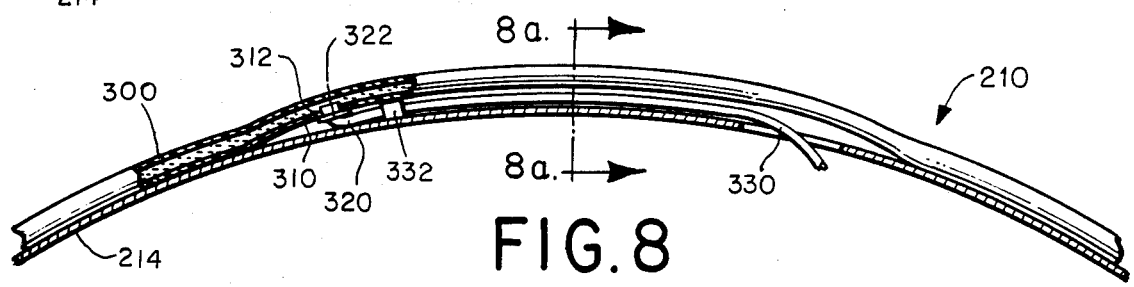
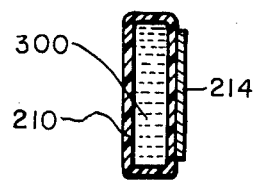
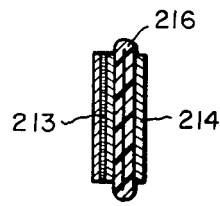
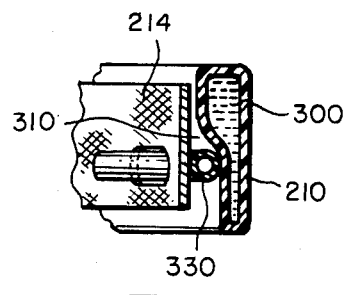
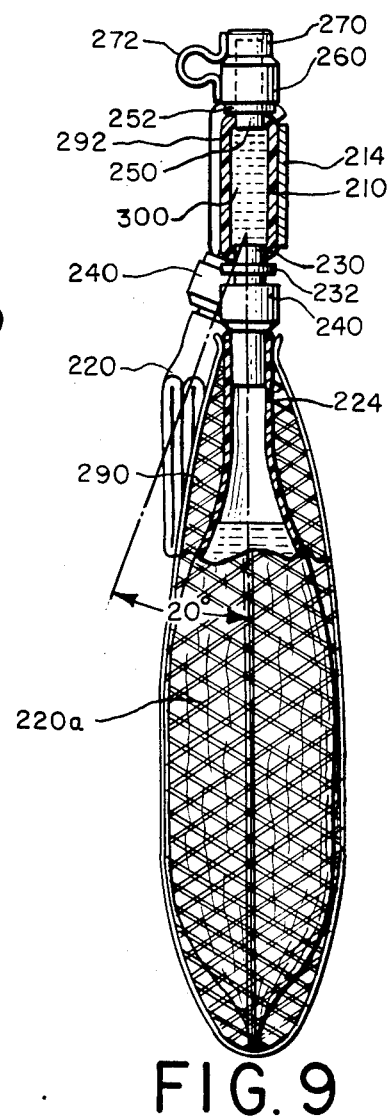

APPARATUS AND METHOD FOR INTRODUCING FLUID INTO AND REMOVING FLUID FROM A LIVING SUBJECT

This Application is a division of pending application Ser. No. 307,188, filed Sept. 30, 1981, and now issued as U.S. Pat. No. 4,435,171, dated 3-6-84. Said application, Ser. No. 307,188 is a continuation application of Ser. No. 45,294, filed June 4, 1979, which was abandoned in favor of the above application, Ser. No. 307,188.

BACKGROUND OF THE INVENTION

The present invention is directed to improved devices and methods for reducing infection associated with the collection of body fluid from a human or animal subject and the introduction of fluids into the body.

In modern medical practice it is often desirable either to drain fluids from or to introduce fluids into a human or animal subject under sterile conditions. For example, it is a routine practice to catheterize hospital patients for urinary or closed wound drainage. Similarly, a number of body cavities, such as the urinary bladder and the peritoneal cavity, for example, are routinely irrigated during treatment of various disorders. In these and other, similar situations the continued sterility of all associated devices used for passing fluid to and from the body may be critically important, for a contaminated device will in many cases lead to infection of the patient.

It is well recognized that conventional drainage devices are a prime source of infection in catheterized patients. For example, in the area of bladder drainage, a large proportion of catheterized patients suffer from urinary tract infections attributable to contaminated drainage devices. In many cases, the drainage collection device itself becomes contaminated in use and infection then ascends in a retrograde manner from the drainage collection device to the patient via the drainage catheter. Such retrograde infection from a contaminated drainage or infusion device has been observed in patients undergoing urinary, wound, biliary, gastro-intestinal drainage, peritoneal dialysis, and hyperalimentation treatment for example. See, e.g., E. M. Goldberg, et al., "Peritoneal Dialysis", *Dialysis and Transplantation*, 1975, 4:50; J. H. Isaacs, et al., "Foley Catheter Drainage Systems and Bladder Damage", *Surgery, Gynecology & Obstetrics*, May 1971, p. 889; R. E. Desautels, "The Causes of Catheter-Induced Urinary Infections and Their Prevention", *J. Urology*, 1969, 101: 757; R. E. Desautels, et al., "Technical Advances in the Prevention of Urinary Tract Infection", *J. Urology*, 1962, 87: 487; R. E. Desautels, "Aseptic Management of Catheter Drainage", *New Eng. J. Med.*, 1960, 263: 189; E. H. Kass, et al., "Prevention of Infection of Urinary Tract in Presence of Indwelling Catheters", *J.A.M.A.*, 1959, 169: 1181; and E. H. Kass, et al., "Entry of Bacteria into the Urinary Tracts of Patients with Inlying Catheters", *New Eng. J. Med.*, 1957, 256: 556.

Retrograde infection via drainage devices is in many cases attributable to the fact that conventional drainage devices are open systems which are repeatedly opened to the atmosphere and, therefore, subject to contamination during use.

Many conventional drainage devices are containers designed to be filled repeatedly with drained body fluid and emptied. For example, the evacuator described by McElhenny in U.S. Pat. No. 3,115,138 includes a capped fluid outlet. After the evacuator becomes filled it is emptied for reuse by removing the cap and expelling collected fluid via the outlet. During this operation the interior of the evacuator is exposed to the atmosphere and contamination of the evacuator may result.

Efforts have been made to reduce the contamination of drainage devices during periodic emptying. For example, U.S. Pat. Nos. 3,779,243 and 3,774,611 disclose evacuators which employ a special valve over the fluid outlet. This valve operates to close the outlet at all times except for the time when fluid is actually being purged from the evacuator. Such evacuators may succeed in reducing the contamination brought on by purging, but they are not true closed systems. Because these evacuators are periodically opened for purging, it is still possible for them to become contaminated and a source of infection.

One object of the present invention is to provide improved drainage devices and methods for reducing the incidence of retrograde infection due to contamination of drainage devices.

In addition to infection due to contamination of drainage devices, a second source of patient infection is contamination of devices for introducing fluid into the body. For example, in peritoneal dialysis large volumes of a dialysate are introduced into and then drained from the peritoneal cavity daily. One conventional approach to this mode of treatment is to use a permanent indwelling catheter and then simply to connect the catheter successively to a series of containers, each of which contains a portion of the total fluid introduced into the body.

In this approach the indwelling catheter is connected to and then disconnected from a number of containers in sequence. The same connection point on the catheter is repeatedly brought into contact with the dialysate and then exposed to the atmosphere. This repeated wetting and exposure to atmosphere is believed to contribute to contamination of the catheter and associated infection. In much the same way, devices for irrigating body cavities such as the bladder may become infected as they are connected to and then disconnected from a number of containers of irrigation fluid in succession.

Thus, a second important object of the present invention is to provide improved devices and methods for introducing fluid into human and animal subjects with reduced possibilities of contamination thereby improving sterility and reducing infection.

SUMMARY OF THE INVENTION

The present invention is directed to improved devices and methods for drawing fluid from and introducing fluid into a human or animal subject, which are less susceptible to contamination and infection than devices and methods of the prior art.

According to a first feature of this invention, a completely closed drainage device is provided in which the interior of the device need never be opened to atmosphere during use. This invention is suitable for widespread use in many types of drainage, and can be used in conjunction with either suction or gravity drainage treatment.

The drainage device of this invention includes a central manifold adapted for connection to a source of body fluid. For example, the manifold may be connected to a drainage catheter which is conventionally located to drain urine from the bladder of a human subject. A plurality of containers are separately connected to the manifold by conduits, and individual conduits are provided with valves which can be positioned to close off the conduits, thereby isolating the associated containers from the manifold. Each of the conduits is severable at a point between the associated valve and container.

In use, this improved drainage device is coupled to a subject so that fluid flows from the patient into the manifold. The valves are positioned to direct the fluid into one of the containers, and fluid is allowed to collect in this container for a period of time. The associated valve is then closed in order to isolate this fluid filled container from the manifold, and the associated conduit is severed between the container and the valve. The fluid filled container is then removed for testing or disposal, and another valve is opened to allow fluid to collect in another container. The separate containers are sequentially filled and removed until either all containers are filled or drainage from the subject is discontinued.

One of the principal advantages of this improved drainage device and method is that each of the multiple containers can be filled and removed from the manifold without ever opening the device to atmosphere during use. When drainage begins the entire device, complete with a number of containers already attached to the manifold, is a sealed, sterile unit. Containers are sequentially filled and removed, but the removal of individual containers is performed only after the respective valve has been closed and the container isolated. Preferably, each valve is capped to further seal it from the environment after the associated container has been removed. In this way contamination of the manifold and resultant infection of the subject are reduced.

Since the drained body fluid is removed in a series of containers of convenient size, the volume of fluid stored in the drainage device at any one time can be kept small in spite of the large total volume of the drainage device. Thus, the patient is not required to carry the total volume of drained fluid. The portability and the convenience of the improved drainage device of this invention provide important advantages over large capacity drainage devices of conventional design.

Furthermore, each of the individual containers can be made of a collapsible material which can be folded into a compact volume for storage before use. In this way a compact drainage device can be made which is readily stored and transported before use, and is relatively low in bulk during use.

This feature of the invention can be advantageously used in urinary drainage, wound drainage, and peritoneal dialysis. It is also well suited for removing other fluids from the body in cases where a low incidence of contamination or infection is important.

According to a second feature of this invention, an improved device for introducing fluid into the human body is provided. This device includes a central manifold adapted for connection with means for introducing fluid into the body, such as a catheter. The manifold includes a plurality of valved input ports. Each port is provided with a separate valve by means of which the port may be isolated from the manifold. Each port is preferably provided with a cap for sealing the port when not in use.

This device is used with a plurality of containers, each of which contains fluid to be introduced into the body. Preferably each container is provided with a dry, sterile catheter and each capped input port is also dry and sterile. To connect the container to the manifold the cap is removed from one of the input ports and then the container catheter is mated to the port. After the catheter is connected, the associated valve is opened and fluid is allowed to flow from the container, through the port, into the manifold, and from there into the body. When the container is emptied, a second container is then connected to the manifold via a second port. In each case the associated port valve is only opened after the container has been connected to the port and the valve is closed before the container is removed. Preferably, each port is only used once so that a fresh, sterile surface on a fresh port is mated to the container catheter each time. By never using a port twice it is believed that the incidence of contamination and infection is reduced.

This second feature of the invention can be advantageously used in irrigation of the bladder, peritoneal dialysis and hyperalimentation treatment, as well as in other modes of treatment in which fluid from several containers must be introduced into the body over a period of time.

Both of the above described features of the invention can be utilized in a dialysis manifold for use in peritoneal dialysis. In this case a central manifold can be provided both with (1) a number of containers connected to the manifold via valved conduits and (2) a number of valved input ports. The dialysis manifold is coupled to the peritoneal cavity of a subject and the separate containers are used as previously described to remove dialysate from the manifold without opening it to the atmosphere. The input ports are also used as described above, thereby reducing infection associated with the introduction of dialysate into the manifold.

Alternately, a manifold for peritoneal dialysis may be constructed with only a plurality of valved ports and the attached containers may be omitted. In this embodiment of the invention containers of dialysate are sequentially coupled to different ports. As before, each port is used only once to reduce infection. In this embodiment, however, a dialysate container is not immediately removed from the associated port after the dialysate has been drained into the peritoneal cavity. Instead, the container is left connected to the port and the dialysate is then drained from the peritoneal cavity into the same container from which it came. It is only then that the container is removed from the port. This embodiment provides the important advantage that the total drainage capacity of the manifold is no longer limited by the number of containers that can conveniently be stored adjacent the manifold.

The invention itself, together with further objects and attendant advantages, will be best understood by reference to the following description taken in connection with the accompanying drawings.

BRIEF DESCRIPTION OF THE DRAWIANGS

FIG. 3 is a perspective view of a portable drainage manifold for urinary drainage.

FIG. 4 is a schematic view of a drainage manifold coupled to a closed wound suction device.

FIG. 5 is a perspective view of a preferred embodiment of an input manifold for wound or bladder irrigation.

FIG. 6 is a perspective view of a first preferred embodiment of a peritoneal dialysis manifold which includes preferred embodiments of both the closed drainage feature and the multiple input port feature of the present invention.

FIG. 7 is a top view taken along line 7—7 of FIG. 6.

FIG. 7a is a cross sectional view taken along line 7a—7a of FIG. 7.

FIG. 7b is a cross sectional view taken along line 7b—7b of FIG. 7.

FIG. 8 is a bottom view taken along line 8—8 of FIG. 6.

FIG. 8a is a cross sectional view taken along line 8a—8a of FIG. 8.

FIG. 9 is a cross sectional view taken along line 9—9 of FIG. 6.

DETAILED DESCRIPTION OF PREFERRED EMBODIMENTS

Figure 1:
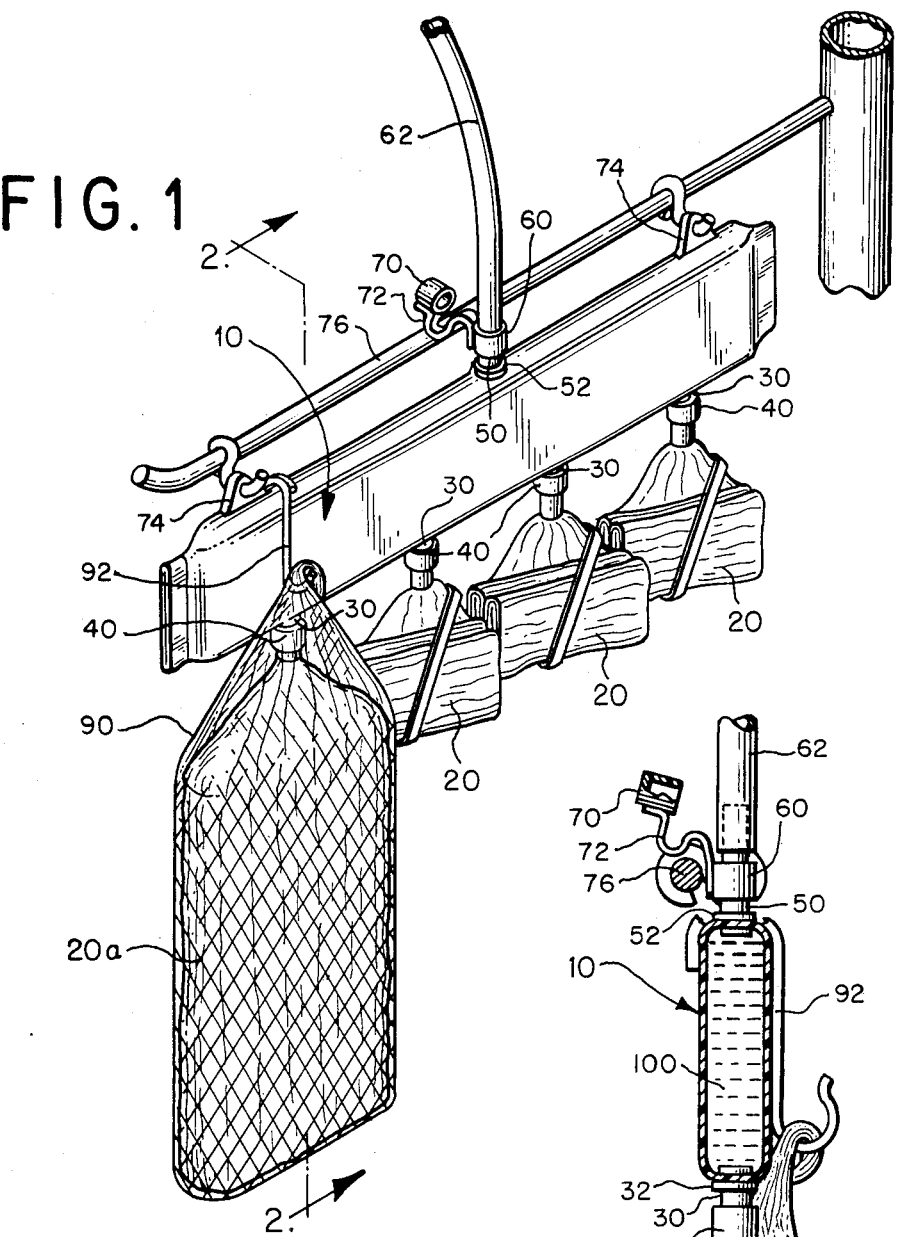
FIG. 1 is a perspective view of a preferred embodiment of a rack mounted drainage manifold for urinary drainage.

Referring now to the drawings, FIG. 1 represents a preferred embodiment of a drainage manifold 10 for urinary drainage. This drainage manifold 10 is a generally tubular structure which is provided with a valved input port 50 and four valved output ports 30. A collapsible, thin walled container 20 is sealed to each of the output ports 30. In FIG. 1, three of these containers 20 are shown collapsed and folded for storage into small packets and one of the containers 20a is shown unfolded, ready to receive fluid from the manifold 10. Preferably, each container is formed of a flexible, plastic material such as vinyl, polyethelene, or some other suitable material. A support net 90 is provided which can be positioned around an unfolded container 20a by means of a hook 92 from the manifold 10. This net 90 serves to support a major part of the weight of fluid contained in the container 20a, thereby permitting the use of thin, low bulk material for the containers 20.

The valved input port 50 is adapted for connection to a catheter 62 which is in turn coupled to a source of body fluid. In this exemplary embodiment, the manifold 10 is a urinary drainage device and the catheter 62 can be any suitable urinary drainage catheter. A snap-on cap 70 is provided adjacent the input port 50 to cover and protect the input port 50 prior to use. Anchor points 74 serve as means for attaching the manifold 10 to any conventional mount such as a rack 76.

Figure 2:
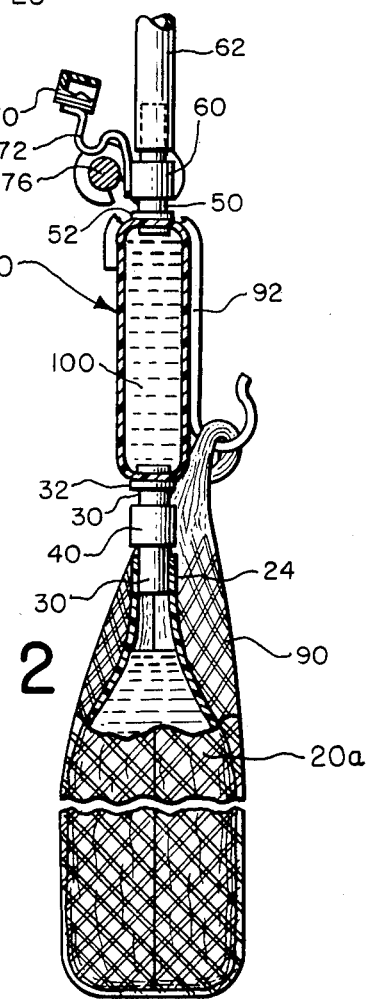
FIG. 2 is a cross sectional view of the drainage manifold of FIG. 1.

Referring now to FIG. 2, the manifold 10 is a tubular structure which defines a central cavity 100. Both ends of the manifold 10 are sealed to prevent leakage and contamination. The input port 50 includes a valve 60 which operates to selectively seal the port 50. The valve 60 is provided with a flange 52 sealed to the manifold 10 and the port 50 extends into the interior of the manifold 10. The cap 70 is attached to the input port 50 via a flexible strap 72.

Each of the valved output ports 30 includes a valve 40 which operates to selectively seal the port 30. Each valve 40 includes a flange 32 sealed to the manifold 10 and each output port 30 extends into the interior of the manifold 10. Each container 20 includes a narrow neck region 24 which is sealed to one of the input ports 30.

The manifold is preferably formed from an extruded tube of vinyl or some other suitable plastic. Standard push-pull valves, such as valve model 320TE manufactured by Halkey-Roberts of Paramus, N.J., are used to reliably seal the associated input ports 50 and output ports 30 against contamination, leakage, and infection. The entire device, including the manifold 10, the foldable containers 20 and the input port 50, forms a single sealed unit which is assembled under standard clean room conditions and then sterilized prior to use. Standard adhesive or heat sealing techniques can be used to bond the manifold 10, the containers 20, and the ports 30,50 together to form a sealed, leakproof unit. Whatever sealing technique is used, however, should provide reliable, leakproof seals which form impermeable barriers to contamination and infection. After assembly, the single opening into the manifold 10 is the valved input port 50, which is closed and capped during the manufacturing process to ensure the continued sterility of the device.

In use, the drainage device of FIGS. 1 and 2 functions as a closed system which receives fluid drained from the body and permits the drained fluid to be removed for disposal without ever opening the drainage device to contamination. As mentioned, the device is originally sterilized with the input port 50 closed and capped. To use this drainage device the input port 50 is uncapped and mated with a suitable catheter under sterile conditions. Depending on the application, this can be done either before or after the catheter has been inserted into the patient. In alternate embodiments, the drainage catheter can be sealed to the input port 50 during the manufacturing process and the entire assembly, including the catheter, can be sterilized as a unit.

After the input port 50 has been mated to the catheter 62 and the catheter 62 has been inserted into the body, the input port valve 60 is opened, one of the containers 20 is unfolded, and the output port valve 40 associated with that container 20 is opened. Fluid then drains from the body, through the catheter, into the manifold 10, and from there into the selected container 20. When this container 20 is filled, the associated valve 40 is closed, and then the filled container is severed from the associated valve 40 and discarded. A second container 20 is then unfolded, the associated valve 40 is opened, and drainage then continues into this second container 20.

Each of the containers 20 is preferably filled in sequence so that no more than one container is receiving drained fluid at any given time. In each case the associated valve 40 is closed before a container 20 is severed, and thus the manifold is never opened to atmosphere or contamination after it has been connected to the source of body fluid. Large quantities of fluid can be drained over an extended period of time without ever opening the system to atmosphere.

The closed system drainage device of this invention has widespread application to a host of situations in which prolonged or large volume drainage is required and a low incidence of infection is important. By way of example, this drainage system can be used in urinary drainage, wound drainage (either with or without wound suction devices), drainage of ascites, drainage of pleural effusion, choledochostomy and T-tube drainage, and pyelo-nephrostomy to drain kidneys. Of course the number and capacity of containers 20 is entirely a matter of choice which should be chosen for the particular application. The embodiment of FIG. 1 is provided with four two-liter bags by way of example, for in urinary drainage the average duration of treatment is less than four days and the average daily urine production is less than two liters. Thus, this embodiment provides a simple, closed system drainage device with adequate capacity for the average case. In situations where drainage is chronic and the avoidance of infection crucial, as in the treatment of some paraplegics, for example, it is preferable to use a closed system drainage device with much larger drainage capacity.

Turning now to FIG. 3, the closed system drainage device of this invention is well suited for use with ambulatory patients. FIG. 3 shows a portable urinary drainage device which is generally similar to that of FIGS. 1–2. As before, a central manifold 10' is provided with a valved input port 50' and four valved output ports 30', each of which is connected to a collapsible container 20'. The input port 50' is adapted for connection with a urinary drainage catheter 62', and the entire assembly, including the manifold 10', the containers 20' and the input port 50', is manufactured as a single sealed unit which is sterilized prior to use.

In this case the two ends 12',14' of the manifold 10' are provided with mating hook-and-loop fasteners such as those marketed under the trade mark "Velcro", and the manifold 10' is sized to fit around the thigh of a patient at a point below the bladder. The weight of the manifold 10' and any suspended containers 20' is supported by straps 16' which connect the manifold 10' to a belt 18' sized to fit around the waist of the patient.

Preferably, each of the output ports 30' is at least ½ inch long, as shown, to permit the port 30' to bend as necessary without closing off as the patient bends his knee in walking and sitting. If desired, each container 20' may be provided with a line 22' at its lower end to hold the containers securely to the leg of the patient. The method of use and the internal structural details of this embodiment are similar to those of FIGS. 1–2.

FIG. 4 shows a schematic view of a closed system drainage device of this invention arranged to receive drainage material from a closed wound suction device 150. Once again, the drainage device includes a manifold 10", a valved input port 50", and several containers 20" connected to the manifold 10" by valved output ports 30". In this application, the drainage device is connected to a suction device 150 via a conduit 152, and the suction device 150 is connected to the body of the patient via a conduit 154.

The suction device 150 can be a conventional closed wound suction device, and it is operated in the conventional manner except that the suction device 150 is periodically emptied through the manifold 10" into one of the attached containers 20" without ever opening either the suction device 150 or the manifold 10" to atmosphere. As before, the closed system drainage device operates to reduce contamination and resulting retrograde infection of the patient.

It should be apparent from the foregoing discussion that the closed system drainage device of this invention can be used either with or without suction devices in either fixed installation or portable embodiments. In alternate embodiments of the invention the manifold can be adapted for particular applications. The manifold can be integrated with a suction device if desired and it can be made in the shape and with the degree of rigidity or flexibility best suited for the particular application.

As previously mentioned, the present invention also includes devices and methods for introducing fluid into the body from multiple sources. In general, these devices include multiple separately valved input ports, each of which is preferably used only once. These devices and methods are well suited for bladder irrigation, wound irrigation, and other situations where sterile fluids are introduced into the body.

Turning now to FIG. 5, a preferred embodiment of the multiple input device of the invention includes an irrigation manifold 130 which may be constructed similarly to the manifold 10 of FIG. 1. This manifold 130 is provided with a single output port 132 adapted for connection with a suitable catheter. This output port 132 is provided with a check valve 134, oriented to prevent fluid from entering the manifold 130 via the output port 132, and a valve 136, which operates to selectively close the output port 132.

The manifold 130 is also provided with a plurality of input ports 140, each of which includes a valve 150 and a snap-on cap 160. Anchor points 138 are included on the manifold 130 to facilitate mounting the manifold 130 to a support structure such as a rack 180.

This irrigation manifold is manufactured under standard clean room conditions. The output port 132 is then closed by means of the valve 136 and capped, each of the input ports 140 is capped and closed by means of the associated valve 150, and then the entire sealed manifold assembly is sterilized.

In use, the output port 132 is coupled to an irrigation catheter, such as a bladder irrigation catheter, for example. As before, the catheter can be made an integral part of the output port 132, or the port 132 can be mated with a suitable catheter either before or after the catheter has been inserted into the body. A container of irrigating solution is then connected to one of the input ports 140 and the associated valve 150 is opened to allow the solution to pass into the manifold 130 and out the output port 132 into the body.

When a second container of nutrient is needed, the valve 150 on the input port 140 connected to the first container is closed and the first container is removed. Then the second container is coupled to a fresh input port 140 that has not previously been used and the process is repeated. Each input port is preferably used only once to reduce the incidence of infection. Of course, normal precautions should be taken to ensure that containers of solution are connected to the input ports 140 under dry, sterile conditions.

The multiple input port feature of the invention is not restricted to use in irrigation. It can be used in many situations where fluid from multiple sources must be introduced into the body under sterile conditions. For example, it may be used in intravenous administration of nutrients and medicines and in hyperalimentation treatment. In each application the size of the manifold and the size and number of the input and output ports should be chosen to fit the intended use. One alternate embodiment of the irrigation manifold 130 of FIG. 5 includes a small, tube-like manifold which attaches directly to the irrigation catheter and includes a small number of valved input ports. In this embodiment, the output port is nothing more than the junction between the manifold and the catheter, and the output port valve can be eliminated. This alternate embodiment is well suited both for collecting samples of body fluid as well as introducing fluid into the body.

Referring now to FIG. 6, both the multiple valved container feature of the invention and the multiple valved input port feature of the invention can be used together in a manifold for peritoneal dialysis. FIG. 6 represents a first preferred embodiment of such a dialysis manifold.

The dialysis manifold of FIG. 6 includes a belt 210 sized to fit around the abdomen of a patient. This belt 210 is a tubular structure which defines a central manifold, as will be shown in greater detail in later figures. The belt 210 is preferably extruded from a flexible plastic material such as vinyl and should have adequate rigidity to prevent the tube of the belt 210 from collapsing during normal use.

A strip of cloth 214 is bonded to the interior surface of the belt, by heat sealing or adhesive bonding, for example. In use, the belt 210 is worn next to the body, and the cloth strip 214 acts to reduce lateral slippage and chafing of the belt against the body.

Four fasteners 212 are secured at spaced intervals to the outside perimeter of the belt 210. In actual use, a lightweight fabric vest 280 is secured to the belt 210 by vest fasteners 282 which couple with the belt fasteners 212. Hook and loop fasteners are preferably used for both sets of fasteners 212 and 282 in this preferred embodiment:. Such fasteners are commonly available under the trade mark "Velcro". The vest 280 serves to support the weight of the belt 210 on the shoulders of the wearer, and it improves the comfort and wearability of the belt 210. In alternate embodiments, suspenders can be substituted for the vest 280; however, for many applications, the vest 280 provides improved long-term wearing comfort as compared with suspenders.

The belt 210 is a single tubular structure which is flattened at the end sections 216,218. Both end sections 216,218 are provided with mating.fasteners, such as hook and loop fastener strips. These fasteners act to secure the two ends of the belt together and to hold the belt in place around the abdomen of the wearer. Hook and loop fasteners provide the advantage of adjustability.

A set of eight containers 220 is mounted on each side of the bottom portion of the belt 210 by means of conduits 230 equipped with valves 240. These containers 220 are preferably thin plastic bags formed from vinyl or polyethelene, for example, which can be compactly folded as shown in FIG. 6 prior to use. Each bag is sealed to the lower end of the associated valve 240 which is in turn sealed to a conduit 230 extending from the belt 210. Adhesives or heat sealing techniques may be used to secure the containers 220, the valves 240, the conduits 230, and the belt 210 to form a single sealed, leakproof unit which provides an impermeable barrier to contamination and infection.

Each of the containers 220 is originally folded into a small packet adjacent the associated valve 240. The use of these containers will be explained in detail below. Here it is enough to note that each container can be unfolded to its full size as shown by the unfolded container 220a. Each container may be of any desired capacity. In the presently preferred embodiment the containers 220 have a capacity of two liters and each container 220 is provided with a volumetric scale 222 by means of which the volume of fluid contained in the container may be estimated.

A support net 290 is secured by means of two hooks 292 to the belt 210 and placed around a container 220a as it is filled. This net bag 290 serves to support a major part of the weight of the fluid in the container 220a, and in this way reduces the strain on the container 220a and the associated valve 240 and conduit 230.

A set of eight input ports 250 is mounted on each side of the top of the belt 210. Each port 250 is a tubular structure which is provided with a valve 260 and a snap-on cap 270. Once again, the ports 250, valves 260, and belt 210 are bonded together to form a single sealed unit which forms an impermeable barrier to infection.

Turning now to FIGS. 7-8, further features of the belt 210 will be explained. FIG. 7 shows a top view of the rear portion of the belt 210 in which the flattened end sections 216,218 and the hook and loop fasteners 213 can be clearly seen. As best shown in FIG. 7a, the belt 210 is a hollow, tubular structure which defines a central volume 300. This central volume is in fluid communication with each of the inlet ports 250 and each of the conduits 230.

FIG. 7b shows a cross section of the belt 210 in the flattened end section 218. In this region the tubular belt 210 has been flattened and two opposed sides of the belt have been sealed together to prevent leakage from or contamination of the belt 210 via the end sections 216,218.

FIG. 8 represents a bottom view of the front portion of the belt 210 in partial cross section. A recess 310 is formed in the lower inside of the front of the belt 210 to house the catheters which couple the belt 210 to the subject. A belt catheter 320 passes through an opening 312 in the belt 210 and is bonded to the belt 210 via a flange 322. Once again, it is important that a leakproof seal be formed to prevent contamination or infection, and heat sealing or adhesive bonding techniques may be used.

The belt catheter 320 is coupled to an indwelling catheter 330 which has previously been inserted into the peritoneal cavity of the subject under sterile conditions. The connection between the belt catheter 320 and the indwelling catheter 330 can be made in any suitable manner, as for example with a female-to-female catheter connector 332.

The recess 310 is sized to receive both the belt catheter 320 and the indwelling catheter 330 when the belt 210 is in place around the patient, as shown in FIGS. 8 and 8a. In this way pressure on the abdomen and attendant discomfort are reduced.

FIG. 9 shows a cross sectional view of the belt 210 showing the internal arrangement of the ports 250 and the container conduits 230. Each conduit 230 penetrates and is in fluid communication with the central volume 300 and is provided with an exterior flange 232 which is sealed against the outside of the belt 210. In order to increase the packing density, adjacent conduits 230 are staggered by about 20°. This permits the folded containers 220 to overlap, as best seen in FIG. 6. Each container 220 defines a narrow neck region 224 which is sealed to the lower portion of the associated valve 240.

Each of the valves 240 is an on-off valve which completely seals off the interior of the belt 210 from infection when the valve 240 is closed. In the presently preferred embodiment, low bulk, push-pull valves are used in which the valve is pulled to open and pushed to close. Such valves are readily available as standard components. Valve model 320TE, manufactured by Halkey-Roberts of Paramus, N.J., is one example of such a valve.

Each of the ports 250 also is in fluid communication with the central volume 300 and is sealed to the exterior of the belt 210 via a flange 252 on the port 250. The port valves 260 are preferably push-pull valves, similar to the container valves 240. The snap-on cap 270 on each valve 260 serves to shield and protect the valve 260 from contamination prior to use. Preferably, each cap 270 is secured to the associated valve 260 by a thin flexible strap 272. The belt 210 should be assembled in a clean room and then sterilized prior to use, utilizing standard manufacturing practices for medical devices as outlined by the Food and Drug Administration. It should be understood that when the belt 210, containers 220, and ports 250 are assembled, all valves 240,260 are closed, and the belt catheter 320 is sealed, prior to sterilization. In this way, the belt is delivered as a single, sterile unit, ready for use.

In use, the belt 210 acts as a manifold through which dialysate can be introduced into and removed from the peritoneal cavity with reduced incidence of infection. The first step in using this belt assembly is to connect the belt catheter 320 to the indwelling catheter 330 of a patient under surgically sterile conditions. This step will usually be performed in the office of the physician or in a hospital.

The next step is the introduction of dialysate into the peritoneal cavity of the patient via the belt 210. First a container of dialysate (not shown) is coupled via a tube to one of the valves 260. The valve 260 will be dry and sterile, for it has been capped since its initial sterilization. The dialysate tube (not shown) should also be dry and sterile. After the dialysate container has been coupled to the valve 260, the valve 260 is opened, and dialysate is allowed to drain via the valve 260 and the port 250 into the central volume 300 of the belt 210. From there, the dialysate passes via the belt catheter 320 and the indwelling catheter 330 into the peritoneal cavity of the subject. After the dialysate container has been emptied, the associated valve 260 is closed, the container is removed, and the cap 270 is replaced. In this way the port 250 is closed by the valve 260 before it is exposed to atmosphere, thereby reducing contamination and infection.

The dialysate is allowed to remain in the peritoneal cavity for a period of time and is then drained from the peritoneal cavity via the belt 210 into one of the containers 220. Prior to this, a selected container is unfolded and placed within the support net 290. The associated valve 240 is then opened and dialysate flows from the central volume 300, via the conduit 230 and the valve 240 into the container 220. After the container is filled, the associated valve 240 is then closed and the filled container 220 is removed from the belt 210 by severing the neck of the bag 220 below the valve 240. The severed container 220 and its contents are then discarded.

Because the container 220 is not removed until after the associated valve 240 has been closed, the belt 210 is never opened to atmosphere during drainage. Instead, the central volume 300 remains closed and uncontaminated.

The next batch of dialysate to be used is then connected to a second inlet port valve 260, one which has not previously been used, and the entire procedure is repeated. In each case a fresh input port 250 and a fresh container 220 are used. Because no input port 250 is used twice, it is always a dry, sterile input port valve 260 which is mated with the dialysate container. When proper precautions are taken to ensure that each dialysate container is sterile, this use of each input port only is believed to reduce the incidence of infection. Furthermore, since all the drainage containers 220 are sealed in place from the beginning, dialysate drainage is accomplished without ever opening the belt 210 to atmosphere. In this way, infection associated with drainage is reduced.

The belt 210 has been designed to minimize infection of the subject from dialysate contamination either when introduced into the subject or when drained. This belt is simple to use and easily portable, and it is anticipated that it will be useful in the treatment of ambulatory patients who are not hospitalized. The patient can administer and drain the dialysate himself, without assistance from medical personnel. Only after each of the ports and containers has been used will the belt be replaced with a new belt, complete with a new set of sterile ports and folded containers.

One current regimen of peritoneal dialysis involves introducing and draining two liter batches of dialysate, four times a day. The belt 210 shown in FIGS. 6–9 is well suited for this regimen, in that it includes 16 ports 250 and 16 two-liter containers 220. This belt 210 can be used for four complete days of dialysis before it will have to be replaced.

Figure 10:
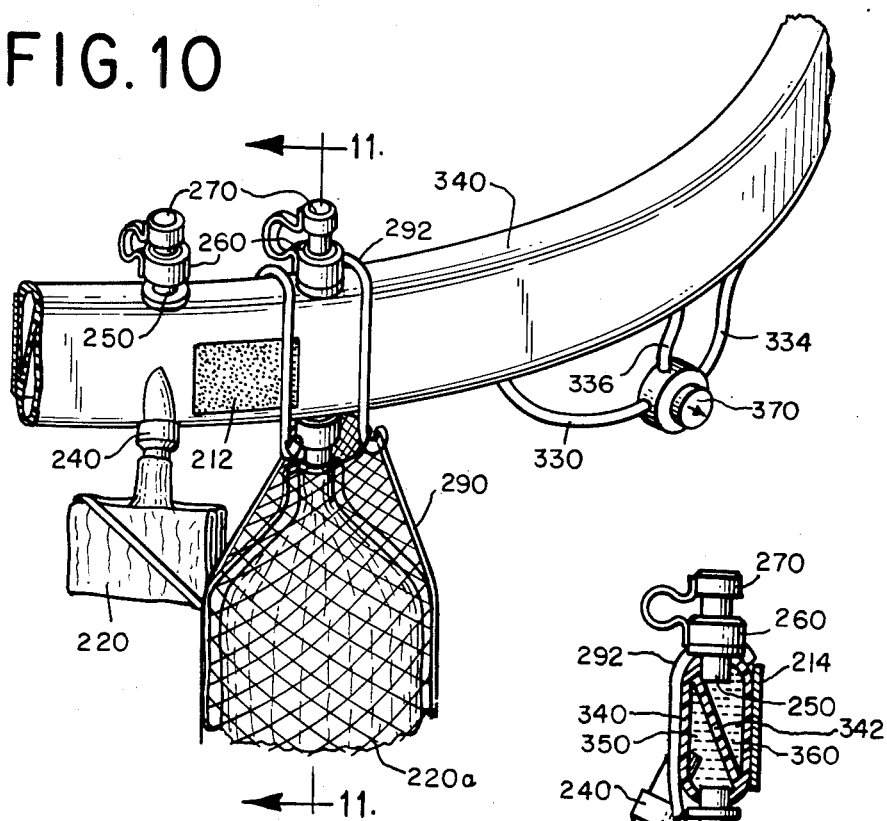
FIG. 10 is a perspective view of a portion of a second preferred embodiment of a peritoneal dialysis manifold.
Figure 11:
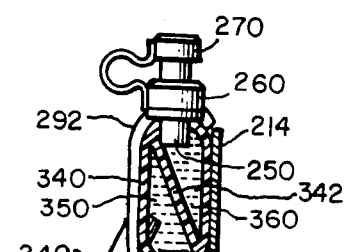
FIG. 11 is a cross sectional view taken along line 11—11 of FIG. 10.

FIGS. 10 and 11 represent a second preferred embodiment of the dialysis belt of this invention. This embodiment is similar to that of FIGS. 6–9 in that it includes 16 valved inlet ports 250 and 16 valved containers 220. For ease of reference, like components of the two embodiments are provided with like reference numbers.

As best shown in FIG. 11, the belt 340 is divided by an internal partition 342 which divides the interior of the belt 340 into two manifolds, or chambers 350,360 which extend the length of the belt 340. The 16 inlet ports 250 all communicate with the inner chamber 360 and the 16 valved containers 220 all communicate with the outer chamber 350 via the valves 240. As shown in FIG. 10, the indwelling catheter 330 is connected to a three-way valve 370 which is in turn coupled both to the inner chamber 360 via an inner belt catheter 334 and to the outer chamber 350 via an outer belt catheter 336. The three-way valve 370 is a standard valve which can be set to a first position to couple the inner belt catheter 334 with the indwelling catheter 330, and to a second portion to couple the outer belt catheter 336 to the indwelling catheter 330. The three-way valve 370 can also be set to close off the indwelling catheter when desired.

The embodiment of FIGS. 10 and 11 is used in much the same manner as that of FIGS. 6–9, except that for introducing dialysate into the peritoneal cavity the three-way valve 370 is set in the first position, which couples the inner belt catheter 334 to the indwelling catheter 330; for draining dialysate valve 370 is set in the second position, which couples the outer belt catheter 336 to the indwelling catheter 330.

A principal advantage of this embodiment is that fresh dialysate is not mixed with previously drained dialysate in the belt 340. In some applications, this may reduce the tendency for compounds leached from the inner walls of the belt 340 by drained dialysate from being introduced into the patient.

Figure 13:
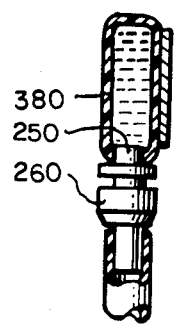
FIG. 13 is a cross sectional view taken along line 13—13 of FIG. 12.
Figure 12:
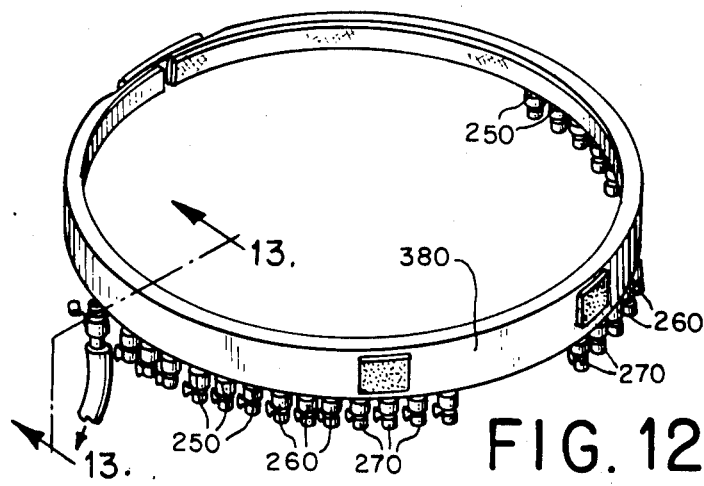
FIG. 12 is a perspective view of a third preferred embodiment of a peritoneal dialysis manifold.

A third preferred embodiment of the dialysis belt of this invention is shown in FIGS. 12 and 13. In this embodiment, the belt 380 defines only a single internal volume. The belt is provided with 28 valved input/output ports 250 arranged along the underside of the belt 380. There are no attached containers in this embodiment. Each of the ports 250 is provided with a valve 260 and a snap-on cap 270 as before, and the belt 380 includes a belt catheter (not shown) similar to that described above in connection with the FIGS. 6-9.

This belt 380 is designed to utilize the dialysate container (not shown) as a drainage container. As before, the belt 380 is originally a sealed sterile unit in which all 28 of the valves 260 are closed. After the belt catheter is coupled to the indwelling catheter (not shown in this view), dialysate is introduced into the belt from a dialysate container which is coupled to one of the input/output ports 250 under sterile conditions. As before, each port 250 is only used once, and each valve 260 is kept closed until after the dialysate container has been connected.

In this case, however, the dialysate container is not removed from the port 250 after the dialysate has been drained into the peritoneal cavity. Instead, the dialysate container is left connected to the port 250 until it is time to drain the dialysate from the peritoneal cavity. Then, without ever removing the dialysate container, the used dialysate is drained into the same container from which it came. After the used dialysate has been returned to its container the associated valve 260 is closed and only then is the filled dialysate container removed from the port 250.

This embodiment provides the important advantages of low bulk and low cost. In that containers need not be sealed to the belt 380 prior to use, more ports 250 can be easily placed around the belt 380. Various numbers of ports may be supplied, depending on the application. The 28 ports of this third preferred embodiment will support a full week of peritoneal dialysis in which four batches of dialysate are introduced and drained daily.

Of course, it should be understood that various changes and modifications to the preferred embodiments described herein will be apparent to those skilled in the art. For example, each of the manifolds can readily be made larger or smaller, or with different fabrication techniques, as required. The size and number of attached containers and input ports can be readily varied to meet the anticipated need, as can the size and type of valves used. Moreover, each form of the invention may be embodied in either portable or nonportable devices, for use with either ambulatory or bedridden patients. Such changes and modifications can be made without departing from the spirit and scope of the present invention and without diminishing its attendant advantages. It is, therefore, intended that such changes and modifications be covered by the following claims.

We claim:

1. A device for introducing dialysate into, and draining dialysate from, the peritoneal cavity of a human subject, said device comprising:
   a first manifold;
   means for transporting dialysate out of the first manifold for introduction into a human peritoneal cavity;
   means for introducing dialysate into the first manifold, said introducing means including a plurality of separately valved input ports;
   a second manifold, isolated from fluid communication with the first manifold;
   means for transporting dialysate from the peritoneal cavity into the second manifold;
   means for receiving dialysate from the second manifold, said receiving means including a plurality of containers individually coupled to the second manifold by means of separately valved conduits; and
   said first and second manifolds being provided in a longitudinally divided, elongated, flexible tubular member that is sized to fit around the abdomen of a human subject.

2. The device of claim 1 wherein the containers are collapsible for compact storage adjacent the second manifold.

3. A method for introducing dialysate into, and draining dialysate from, the peritoneal cavity of a human subject, said method comprising the steps of:
   (a) coupling a dialysis manifold to the peritoneal cavity of a human subject such that the manifold is in fluid communication with the peritoneal cavity, said manifold including a plurality of input/output ports in fluid communication with the manifold, each of said ports including a valve operative to selectively isolate the associated port from the manifold;
   (b) coupling a container of dialysate to a preselected port;
   (c) opening the valve associated with the preselected port to permit dialysate to flow into the manifold via the preselected port, and from the manifold into the peritoneal cavity;
   (d) maintaining the container connected to the preselected port while the dialysate is in the peritoneal cavity;
   (e) draining the dialysate from the peritoneal cavity back into the container via the manifold and the preselected port;
   (f) closing the valve associated with the preselected port prior to removal of the container from the preselected port; and
   (g) repeating steps (b) through (f) with another container of dialysate and another preselected port which has not previously been used.

4. A method for introducing dialysate into, and draining dialysate from, the peritoneal cavity of a human subject, said method comprising the steps of:
   (a) coupling a dialysis manifold to the peritoneal cavity of a human subject such that the manifold is in fluid communication with the peritoneal cavity, said manifold including a plurality of input ports in fluid communication with the manifold, each of said ports including a valve operative to selectively isolate the associated port from the manifold, said manifold also including a plurality of containers in fluid communication with the manifold, each of said containers including a valve operative to selectively isolate the manifold from the associated container;
   (b) coupling a source of dialysate to a preselected port;
   (c) opening the valve associated with the preselected port to permit dialysate to flow into the manifold via the preselected port, and from the manifold into the peritoneal cavity;
   (d) closing the valve associated with the preselected port before removing the source of dialysate therefrom;
   (e) opening the valve associated with a preselected container and allowing dialysate to drain from the peritoneal cavity into the preselected container via the manifold;
   (f) closing the valve associated with the preselected container prior to removal of the preselected container from the manifold to substantially prevent contamination of the manifold;

(g) removing the preselected container from the manifold while leaving the closed valve associated with the preselected container in place adjacent the manifold; and (h) repeating steps (b) through (g) with another source of dialysate and another, unused input port.

5. A method for introducing dialysate into, and draining dialysate from, the peritoneal cavity of a human subject, said method comprising the steps of:

(a) coupling first and second dialysis manifolds to the peritoneal cavity of a human subject such that both manifolds are alternately in fluid communication with the peritoneal cavity, said first manifold including a plurality of input ports in fluid communication with the first manifold, each of said ports including a valve operative to selectively isolate the associated port from the first manifold, said second manifold including a plurality of containers in fluid communication with the second manifold, each of said containers including a valve operative to selectively isolate the second manifold from the associated container;

(b) coupling a source of dialysate to a preselected port;

(c) opening the valve associated with the preselected port to permit dialysate to flow into the first manifold via the preselected port, and from the first manifold into the peritoneal cavity;

(d) closing the valve associated with the preselected port before removing the source of dialysate therefrom;

(e) opening the valve associated with a preselected container and allowing dialysate to drain from the peritoneal cavity into the preselected container via the second manifold;

(f) closing the valve associated with the preselected container prior to removal of the preselected container from the second manifold to substantially prevent contamination of the second manifold;

(g) removing the preselected container from the second manifold while leaving the closed valve associated with the preselected container in place adjacent the second manifold; and (h) repeating steps (b) through (g) with another source of dialysate and another, unused input port.

* * * * *